United States Patent
Chilese et al.

(10) Patent No.: US 7,050,170 B2
(45) Date of Patent: May 23, 2006

(54) APPARATUS AND METHOD FOR MAINTAINING UNIFORM AND STABLE TEMPERATURE FOR CAVITY ENHANCED OPTICAL SPECTROSCOPY

(75) Inventors: Frank Chilese, San Ramon, CA (US); Bernard Fidric, Cupertino, CA (US)

(73) Assignee: Picarro, Inc., Sunnyvale, CA (US)

( * ) Notice: Subject to any disclaimer, the term of this patent is extended or adjusted under 35 U.S.C. 154(b) by 396 days.

(21) Appl. No.: 10/625,231

(22) Filed: Jul. 22, 2003

(65) Prior Publication Data
US 2005/0018193 A1    Jan. 27, 2005

(51) Int. Cl.
*G01N 21/61*    (2006.01)
(52) U.S. Cl. .................. 356/437; 356/440; 250/352
(58) Field of Classification Search .............. 356/436, 356/437, 440, 246; 250/343, 352
See application file for complete search history.

(56) References Cited

U.S. PATENT DOCUMENTS

| | | | |
|---|---|---|---|
| 3,860,818 A * | 1/1975 | Stalder et al. | 250/343 |
| 4,749,276 A * | 6/1988 | Bragg et al. | 250/352 |
| 5,320,808 A * | 6/1994 | Holen et al. | 356/246 |
| 6,486,474 B1 * | 11/2002 | Owen et al. | 356/440 |
| 2004/0211905 A1 * | 10/2004 | Hancock et al. | 250/343 |

* cited by examiner

*Primary Examiner*—Richard A. Rosenberger
(74) *Attorney, Agent, or Firm*—Lumen Intellectual Property Services, Inc.

(57) ABSTRACT

An enclosure for a cavity enhanced optical spectroscopy instrument provides a highly temperature stable environment by positioning the instrument optical cavity away from the enclosure walls and providing a wall mounted heat pump, fan and heat exchanger. The fan causes the gas contained within the enclosure to circulate over the heat exchanger and in a laminar, non-turbulent flow path along interior wall surfaces of the enclosure thereby maintaining the optical cavity in a temperature and vibration stable zone.

12 Claims, 4 Drawing Sheets

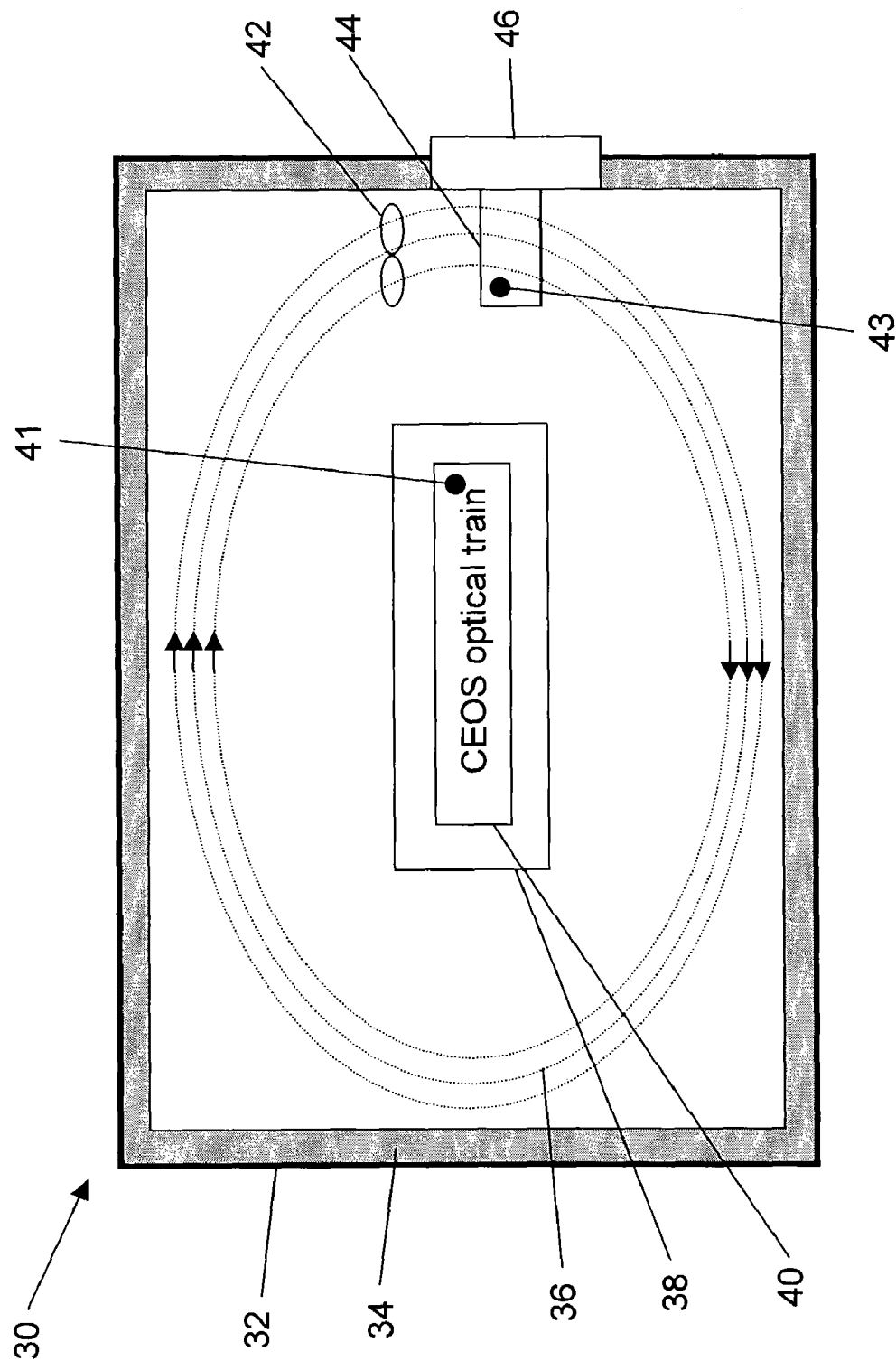

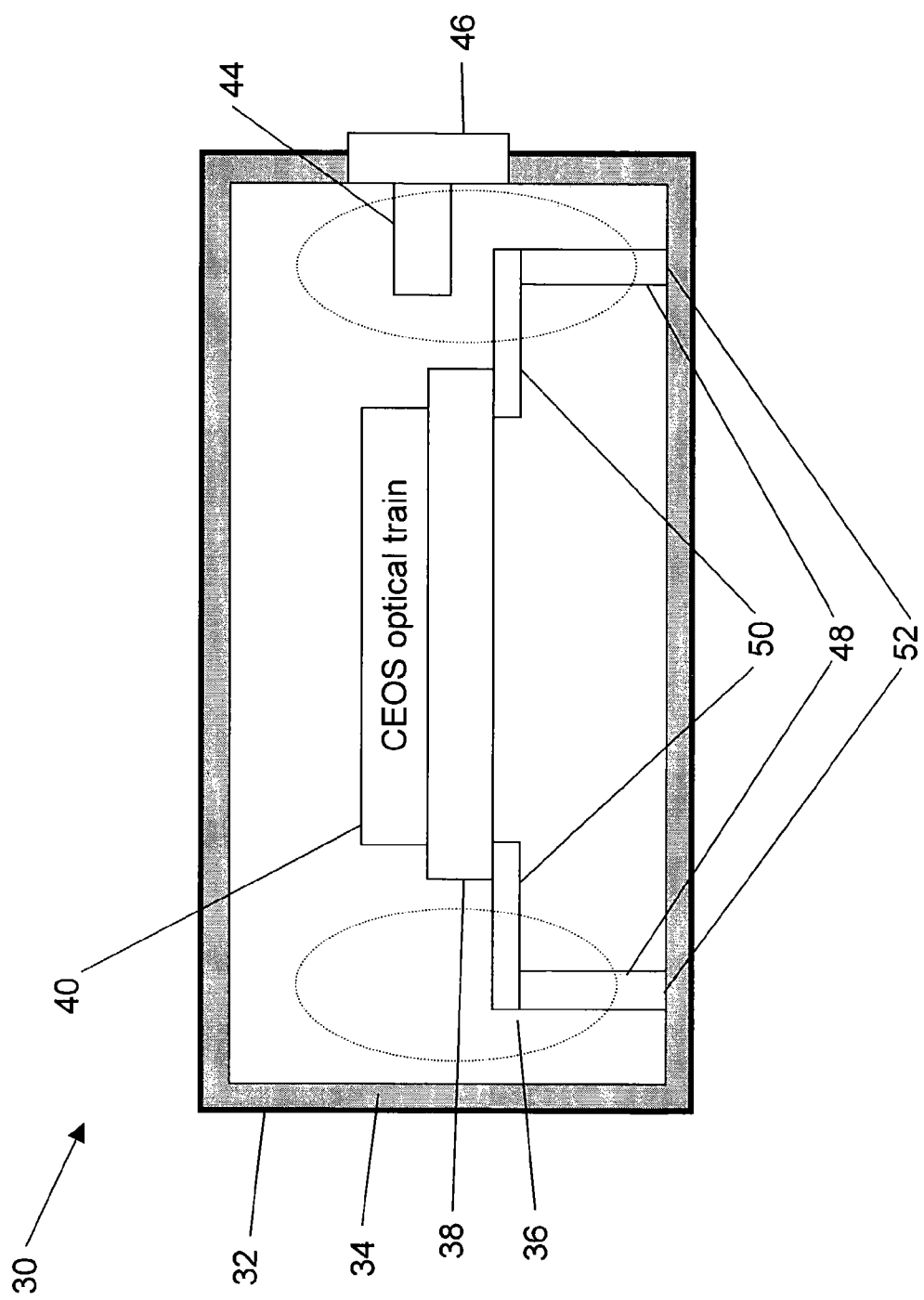

APPARATUS AND METHOD FOR MAINTAINING UNIFORM AND STABLE TEMPERATURE FOR CAVITY ENHANCED OPTICAL SPECTROSCOPY

FIELD OF THE INVENTION

The present invention relates to an improved design for cavity enhanced optical spectroscopy (CEOS) instruments. The improvement comprises a unique chamber or enclosure designed to maintain the optical resonator, and preferably the entire optical train, of a CEOS instrument at a highly uniform and stable operating temperature.

BACKGROUND

Cavity enhanced optical spectroscopy (CEOS) entails the use of a passive optical resonator, also referred to as an optical cavity, to improve the performance of an optical spectroscopy instrument. Cavity enhanced absorption spectroscopy (CEAS), and cavity ring down spectroscopy (CRDS) are two of the most widely used CEOS techniques. The intensity of single-mode radiation trapped within a passive optical resonator decays exponentially over time, with a time constant $\tau$ which is often referred to as the ring-down time. In practice, it is preferable to ensure that only a single resonator mode has an appreciable amplitude, since excitation of multiple resonator modes leads to multi-exponential radiation intensity decay (i.e., multiple time constants), which significantly complicates the interpretation of measurement results. The ring-down time $\tau$ depends on the cavity round trip length and on the total round-trip loss within the cavity, including loss due to absorption and/or scattering by a sample present in the cavity. Thus, measurement of the ring-down time of an optical resonator provides spectroscopic information on a sample within the resonator, and both CRDS and CEAS are based on such a measurement of $\tau$.

In CRDS, an optical source is coupled to the resonator in a mode-matched manner, so that the radiation trapped within the resonator is substantially in a single spatial mode. The coupling between the source and the resonator is then interrupted (e.g., by blocking the source radiation, or by altering the spectral overlap between the source radiation and the excited resonator mode). Typically, a detector is positioned to receive a portion of the radiation leaking from the resonator, which decays in time exponentially with time constant $\tau$. The time-dependent signal from this detector is then processed to determine $\tau$ (e.g., by sampling the detector signal and applying a suitable curve-fitting method to a decaying portion of the sampled signal). Note that CRDS entails an absolute measurement of $\tau$. The articles in the book "Cavity-Ringdown Spectroscopy" by K. W. Busch and M. A. Busch, ACS Symposium Series No. 720, 1999 ISBN 0-8412-3600-3, including their cited references, cover most currently reported aspects of CRDS technology.

Single spatial mode excitation of the resonator is also usually employed in CEAS, (sometimes called integrated cavity output spectroscopy (ICOS)), but CEAS differs from CRDS in that the wavelength of the source is swept (i.e., varied over time), so that the source wavelength coincides briefly with the resonant wavelengths of a succession of resonator modes. A detector is positioned to receive radiation leaking from the resonator, and the signal from the detector is preferably integrated for a time comparable to the time it takes the source wavelength to scan across a sample spectral line of interest. The resulting detector signal is proportional to $\tau$, so the variation of this signal with source wavelength provides spectral information on the sample. Note that CEAS entails a relative measurement of $\tau$. The Ph.D. dissertation "Cavity Enhanced Absorption Spectroscopy", R. Peeters, Katholieke Universiteit Nijmegen, The Netherlands, 2001, ISBN 90-9014628-8, provides further information on CEAS and CRDS technology and applications. The Peeters dissertation focuses primarily on the use of lasers (either pulsed or CW) as the light source for CEOS instruments. However, an article by Fiedler et. al., Chemical Physics Letters 371 (2003) 284–294 teaches that an incoherent light source e.g., a xenon arc lamp is also suitable for cavity-enhanced absorption spectroscopy. Other incoherent sources are also suitable e.g., LEDs.

Independent of the light source selected, achieving maximum performance from CEOS instruments requires that the optical cavity (and preferably the entire optical train) be maintained at a uniform and stable temperature with minimal environmental perturbation (e.g., vibration) during the course of an analysis. Temperature sensitivity of the operating frequency is characteristic of all electromagnetic and acoustic resonators, including lasers, due to thermally induced variations in the size, dielectric constants, speed of sound, etc., for solid-state materials. Fractional variations of these parameters is typically $10^{-4}$ to $10^{-5}$ parts per degree Kelvin. If the sample being analyzed is a liquid, its index of refraction will change with temperature which change can produce drift and/or inaccuracy in measurement. When CRDS or CEAS is being used to determine gas isotope ratios e.g., $C_{14}O_2$ vs. $C_{12}O_2$, a change in temperature can affect the Boltzman distribution for the different isotopes and hence change the measured isotope ratio for a fixed composition.

There is currently a need for a highly sensitive and accurate CEOS instrument that is also sturdy, portable and can be moved relatively easily so as to permit, for example, multi-location pollution monitoring or explosive detection. Such an instrument may be exposed to a rapidly varying ambient temperature, as well as other environmental perturbations such as vibrations, so isolating a CEOS instrument from the ambient environment, both thermal and vibrational, is highly desirable. Although current CEOS instruments frequently place the optical train, or at least the optical cavity, in some type of enclosure to reduce the influence of the ambient environment, current designs are inadequate in these respects.

U.S. Pat. No. 5,692,556 describes a temperature controlled test chamber for electronic components where the air temperature variation in the chamber can reportedly be maintained in the milli-Kelvin range. A critical aspect of the design of this chamber is ensuring a turbulent air flow pattern throughout the chamber. The basic premise is that by moving the air as rapidly as possible throughout all parts of the enclosure in a turbulent flow, a uniform temperature will be achieved throughout the chamber. While it is true that turbulent air flow within a chamber generally affords low internal temperature gradients, such turbulent flow also tends to rapidly transfer heat from (or to) the ambient air outside the enclosure to the internal components. As indicated, a critical aspect of CEOS is that the temperature of the instrument remain constant during the course of an analysis. It is less important that it remain at a particular temperature. In addition to the inherent problem of the impact of rapidly moving air on delicate optical components within the enclosure, (note that, in general, the greater the flow rate, the greater the level of impact) we have found that a turbulent flow approach is incapable of maintaining the temperature within the enclosure (and hence the temperature of the optical train) within the very narrow range necessary to obtain the maximum sensitivity and selectivity of which CRDS or CEAS is capable. For utmost accuracy in spectroscopic measurement, we have found it desirable to maintain the temperature of the optical train within the range of ±0.01 K, more preferably ±0.001K. Existing enclosure designs have not demonstrated this level of performance.

SUMMARY

We have unexpectedly found that the provision of a slow, laminar flow of gas along the inner wall surface of the enclosure, thereby providing a central "dead zone" of very limited gas movement in the enclosure interior, i.e., in the region surrounding the optical train, provides a highly thermally stable and vibration free environment for the optical train, thereby enabling highly reproducible and accurate spectroscopic results to be obtained with CRDS and CEAS instruments. The term "laminar flow" as used herein indicates that the laminar flow region is substantially free from turbulent flow and that the majority of the molecules of the circulating gas move in a direction substantially parallel to each other and to the inner wall surfaces of the enclosure. Obviously at the corners of the enclosure, and immediately after being impelled by the fan, the molecules will not be moving precisely parallel to a wall surface. An important aspect of the present invention is that there is essentially a boundary between the dead zone and the flowing gas so that at most very limited mixing of the laminar flow gas and the dead zone gas occurs. Gases other than dry air can be used to practice the invention although dry air is normally the gas of choice.

It should be realized that a CEOS instrument is expected to operate under service conditions where there may be considerable variation in the ambient temperature outside the enclosure during the course of a spectrographic analysis. Such ambient temperature variations must not be allowed, to the maximum extent possible, to affect the temperature of the gas inside the enclosure and, in particular, the temperature of the optical train.

The point to be born in mind is that accuracy of measurement is primarily dependant on the optical train being maintained at a uniform temperature throughout the course of an analysis. The ability to exactly achieve a particular temperature is of less importance. In addition to precise temperature control, the enclosure design of the present invention affords excellent protection from vibration of the optical train (also called "air wiggle" or "optical jitter"), which is also a critical aspect of providing accurate analyses.

BRIEF DESCRIPTION OF THE DRAWINGS

FIG. 2a schematically shows a top view of an enclosure according to the present invention.

FIG. 3 schematically shows a side view of an alternative design for the optical bench mounts for use in an enclosure of the present invention.

DETAILED DESCRIPTION OF THE DRAWINGS

Figure 1:
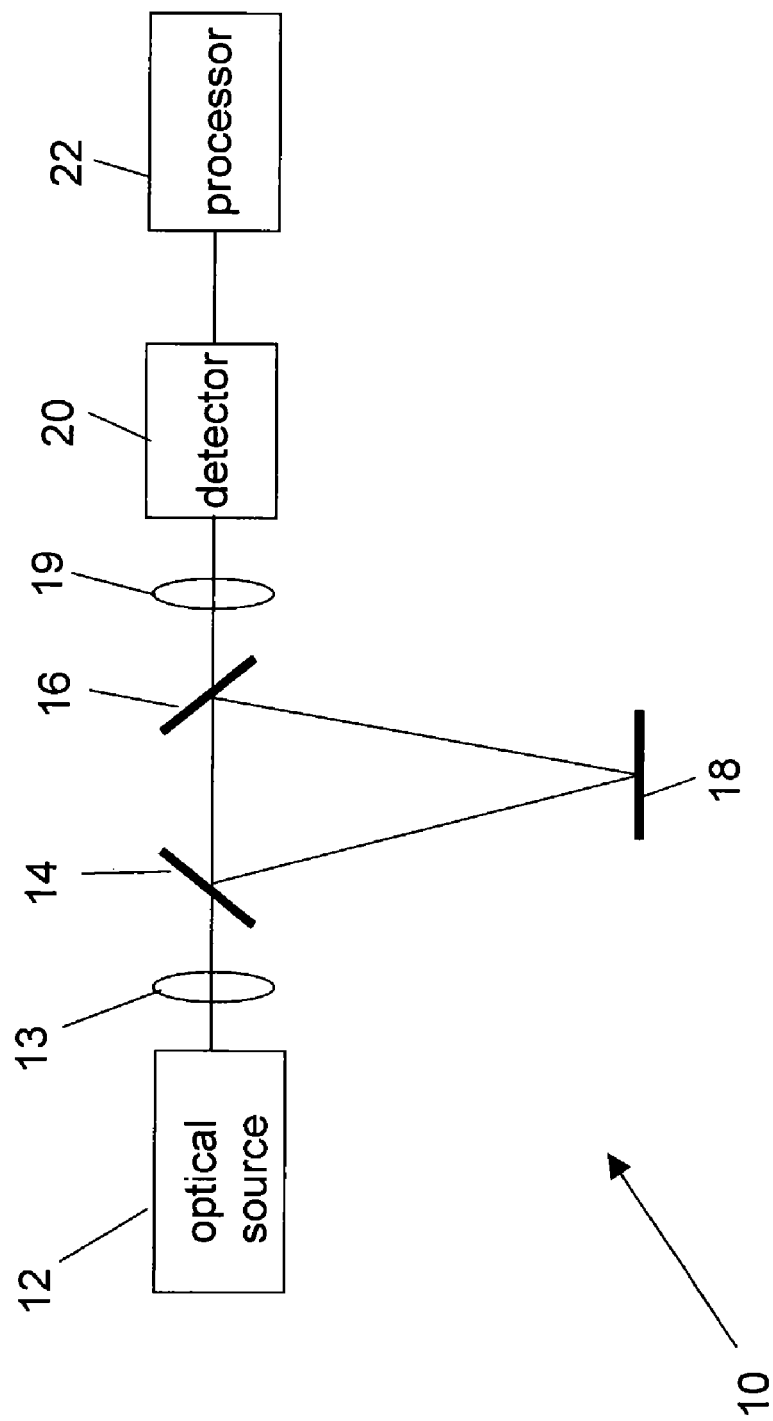
FIG. 1 schematically shows a typical CEOS instrument.

FIG. 1 schematically shows a CEOS instrument 10, which, as indicated above, can be either a CRDS instrument or a CEAS instrument. A CEOS instrument normally includes at least the following components: a) an optical cavity containing two to four planar or curved mirrors (a three mirror cavity, with mirrors numbered 14, 16 and 18, is shown here); b) optical source 12, which is typically either a pulsed laser or a continuous wave laser (although as noted above source 12 can also be an incoherent source); c) mode matching optics 13 located between the laser and the optical cavity to mode match the laser to the cavity; d) detector or detector array 20, which receives radiation emitted by the cavity; e) transfer optics 19 located between the cavity and the detector to focus the light emitted from the cavity onto the detector; and f) processor 22, which processes the signal received by the detector to provide measurement results. A detector array is frequently appropriate when the light source is an incoherent source as opposed to a laser. Components a) through e) i.e. components 12 through 20 of FIG. 1, are normally referred to as the optical train. The components of a CEOS instrument are typically positioned on support means which can be any substantially rigid planar surface (normally called an "optical bench" or "bread board" and not shown in this Figure). Such optical benches are preferably of high thermal mass and conductivity to help maintain the optical train at a stable and uniform temperature, and hence are normally fabricated at least principally of metal. The optical cavity (sometimes called the ring-down cavity or the resonant cavity) comprises a glass or metal tubular container for the sample, which can be a gas, a liquid or a vapor, e.g., a gas containing dispersed particulate matter and/or aerosol droplets, such as normal atmospheric air or stack gases. Additionally, the cavity will usually include sample inlet and outlet means.

FIG. 2a is schematic top view of an enclosure 30 according to the present invention having a CEOS instrument optical train 40 centrally located therein. In FIG. 2a, No. 32 indicates the enclosure wall and No. 34 an inner insulating layer. Although enclosure wall 32 is illustrated as having an essentially rectangular configuration, which is generally the shape most easily fabricated, this is not a critical aspect of the invention. The enclosure can, for example, be of square, ovoid or other geometry. The important factor is that it be of a size and configuration to enable laminar gas flow and to permit the optical cavity, and preferably the complete optical train, of a CEOS instrument to be situated in a dead zone of the gas flow. Enclosure wall 32 is most conveniently fabricated of metal, although stiff plastic (e.g., Plexiglas or fiberglass reinforced epoxy) or a combination of metal and plastic may alternatively be used. Plastic has the advantage of being less thermally conductive than metal. Advantageously, at least a substantial portion of the surface of the inner and/or outer walls of the container will be covered with a low thermal conductivity insulating material, shown as No. 34 on the Figure. Most advantageously, this material will have both insulating and vibration damping characteristics, such as is provided by certain urethane foams. Other suitable foams include, for example, vinyl/nitrile copolymer closed cell foams. An additional or alternative insulating layer can be situated on the outer wall surface of enclosure wall 32.

No. 36 shows the laminar flow of the gas (normally dry air) as it circulates within the enclosure. CEOS instrument optical train 40 is located within a "dead zone" encircled by laminar flow 36. Although the gas flow within the dead zone is generally not exactly zero, the gas flow speed within the dead zone is sufficiently low compared to the flow speed of laminar flow 36 that the gas in the dead zone can be regarded as being essentially static. Thus, the dead zone is not regarded as part of laminar flow 36, and so CEOS instrument optical train 40 is not within the path of laminar flow 36. No. 38 indicates the optical bench on which the components of CEOS instrument 40 are mounted. Optical bench 38 will normally be connected to an interior floor surface of enclosure 30 through a plurality of preferably vibration damping mounts which also provide thermal isolation between the bench and the floor of the enclosure.

The fan is indicated as No. 42, and is mounted so as to circulate the gas present within the enclosure in a laminar flow 36 across heat exchanger 44 and substantially along some of the interior wall surfaces of the enclosure. In the example of FIG. 2, the path of laminar flow 36 is substantially along four of the interior wall surfaces of enclosure 30, and is not substantially along the top or bottom of enclosure 30. Fan 42 is preferably an electric fan rotating at a relatively low speed. We have found that DC motors are preferable in fan 42 to AC motors, as DC motors permit facile control of the fan speed by merely raising or lowering the motor input voltage. In addition, DC motors tend to be less prone to vibration, especially at lower speeds. Heat exchanger 44 is normally a multi-finned metal structure mounted within the enclosure, in thermal communication with (and preferably affixed to) heat pump 46. Heat pump 46 is typically mounted to a wall of enclosure 30, and is in thermal communication with heat exchanger 44 and also with the ambient environment outside enclosure 30. On FIG. 2a, heat pump 46 is shown as being situated in an aperture which passes through enclosure wall 32 and insulating layer 34. Heat pump 46 acts to transfer heat from the exterior to the interior of enclosure 30 (or in some circumstances vice versa). It is preferable for maximum flexibility for heat pump 46 to be a thermoelectric cooler/heater based on the Peltier Effect so that it can remove as well as add heat to the interior gas, although other mechanisms for transferring heat are also suitable for practicing the invention. For example, if it is certain that the exterior environment temperature will always be sufficiently low that heat will invariably have to be added to the interior gas during an analysis, then a simple resistive heater will be suitable and it is intended that the term "heat pump" encompass a resistance heater.

Heat pump 46 can be mounted on the inner or outer wall surface of enclosure 30, or may be mounted in a wall orifice so that the heat pump passes through the enclosure wall. The important factor is that heat pump 46 be in thermal communication with both the outside ambient air and also with the inside heat exchanger 44 so as to enable the heat exchanger to heat (or cool) the adjacent internal gas as may be necessary to accommodate any temperature change in the external environment. In a preferred embodiment, there will be at least two heat pumps, fans and heat exchangers, all of which may be mounted on the same, adjacent or preferably opposite sides of the enclosure. Multiple heat pumps, exchangers and fans are preferred so that the circulating gas need not move very far before coming into contact with a heat exchanger. If plural heat pumps are used, they are preferably wired in series so as to function essentially as a single unit.

Also shown on FIG. 2a are temperature sensor 41 and temperature sensor 43. Temperature sensor 43 is optional, although it is present in a preferred embodiment of the invention. Temperature sensor 41 is preferably affixed to an exterior surface of the optical cavity of CEOS instrument optical train 40. An alternative arrangement, not shown on FIG. 2a, is to affix temperature sensor 41 to optical bench 38. Under some circumstances it may be desirable to affix temperature sensors to both the optical cavity and the optical bench. Temperature sensor 41 is connected to an external control circuit which activates heat pump 46. Suitable temperature sensors include thermocouples, resistive thermal devices and preferably thermistors.

As indicated, the critical factor in providing accurate spectroscopic analysis is maintaining the optical cavity, and preferably the entire optical train, at a constant temperature. In theory, one would need only to monitor the temperature of the optical cavity (e.g., with temperature sensor 41) and, as necessary, instruct the heat pump to add (or remove) heat via the heat exchanger to maintain the optical cavity at a constant temperature. Such operations can be performed with a thermal controller (not shown on the Figure). In practice, we have found that a preferred approach is to use at least two thermistors (or other temperature sensors), one mounted on the optical cavity (i.e., temperature sensor 41) and a second on a heat exchanger (i.e., temperature sensor 43). The advantage of this approach may be more easily understood if we consider several factors that are normally present when the CEOS instrument is in operation: 1) the preferred operating temperature of the optical cavity, and preferably the entire optical train, will normally be higher than that of the ambient air outside the enclosure; 2) the thermal mass of the optical train and of the optical bench supporting same will be much greater than that of the heat exchanger; 3) the optical train and the optical bench will be at essentially the same temperature; 4) the optical train will generate some heat when in operation; and 5) there will be limited, but not zero, thermal communication from the outside ambient environment to the optical bench and train, for example, through the bench mounts.

If one starts with the enclosure and its contents (i.e., optical bench, optical train, fans, heat exchangers and heat pump) all at ambient temperature, e.g. 25° C., and then begins to raise the optical bench and train up to a desired operating temperature of, e.g. 40° C., one proceeds as follows when using two temperature sensors. With the laser turned on, the heat pump or pumps will input heat to the heat exchanger and the fan will cause laminar gas flow over the heat exchanger. Since the rate of heat transfer to the dead zone and thence to the bench and train is limited, and the thermal mass of the optical bench and train is high, bringing these components up to about 40° C. will take some time. As previously pointed out, it is not critical that the optical train be at exactly 40° C. (or some other selected operating temperature) but rather that its temperature not vary by more than ±0.01K, preferably not more than ±0.001K during an analysis. When the train and bench reach the desired temperature T1, as indicated by the temperature sensor 41, the thermal controller will recognize this temperature as a first set point and thereafter detect any change from temperature T1 by the optical train.

The thermal controller will also recognize the temperature T2 of the heat exchanger (say 41° C.), as indicated by temperature sensor 43, which is necessary to bring the optical bench and train to T1 and maintain them at T1 in the absence of a thermal change in the external environment. This heat exchanger temperature will be recognized by the controller as a second set point. Again the exact temperature of the second set point is not critical but rather that the temperature controller can determine whether to input or withdraw heat to move the temperature of the heat exchanger up or down from this set point as a result of even a very small change in T1. Since the temperature of the bench and train will only change slowly and to a very limited extent because of their thermal mass and location in the dead zone, as soon as any change from the first set point is detected (e.g. a slight decrease in temperature T1), the controller will instruct the heat pump to raise the temperature of the heat exchanger above T2. The heat exchanger has low thermal mass and will heat rapidly and will likewise rapidly heat the circulating gas flowing over it, which will, even allowing for the limited heat transfer from the laminar flow gas to the dead zone gas, cause the temperature of the dead zone gas and hence of the optical bench and train to rise back to T1 before the bench and train have had the opportunity to fall below T1 to any significant extent, e.g., by more than 0.001° C.

Figure 2B:
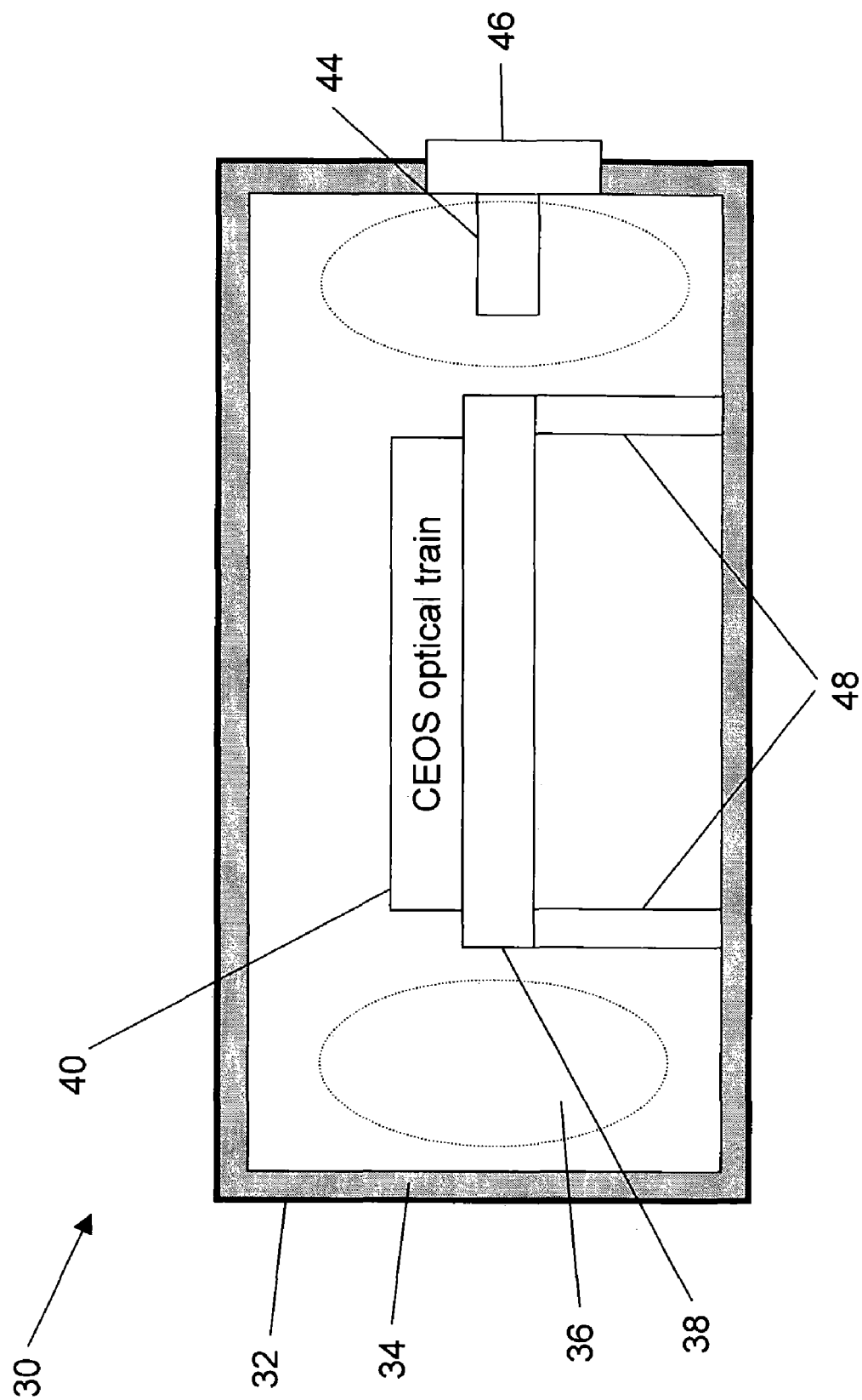
FIG. 2b schematically shows a side view of an enclosure according to the present invention.

FIG. 2b is a schematic side view of the same chamber as shown in FIG. 2a and like numbers denote like components. Vertical support mounts 48 for the optical bench are shown on FIG. 2b. These mounts serve to provide both thermal and vibrational insulation of optical bench 38 and CEOS instrument optical train 40 from environmental perturbations.

FIG. 3 shows an alternative embodiment for the optical bench mounts. In this case, vertical support mounts 48 are not situated directly beneath bench 38. Rather, there are horizontal struts 50 which project outwardly from bench 38 to connect (or be integral) with support mounts 48. An advantage of this particular configuration is that it minimizes the effects of any heat transfer from the bench to the outside environment through the container walls at points 52 where the bench mounts contact the floor of the enclosure. This reduction in heat transfer is because the connection points of the bench to the supports are held at a temperature close to T1 by the circulating air, so there is no temperature difference to drive heat flow.

An advantage of our enclosure design is that in order to affect the temperature of the optical train, a change in the ambient temperature outside the enclosure must be communicated through the enclosure walls, including through any insulating layers present thereon, and thence to the circulating gas (except for minimal transfer through the bench mounts). Since the dead zone gas surrounding the optical train is substantially static, any heat transfer to or from the dead zone can occur only be at the interface of the circulating laminar flow gas and the dead zone gas. Heat transfer to the optical train from the circulating gas can thus only be via conduction through the dead zone. Since gases are typically of low thermal conductivity, and since laminar flow is low friction flow relative to turbulent flow, the layers of circulating air between the walls and the dead zone can appropriately be thought of as providing "active insulation" to the optical train and bench. An additional benefit of our current enclosure design is that since any outside temperature change only impinges on the circulating gas, only a comparatively small portion of the gas within the enclosure (the circulating gas) needs to be directly heated (or cooled) by the heat pump.

It should be noted that theoretically, to achieve high precision, only the actual optical cavity itself needs to have its temperature uniformly maintained and hence only this component of the optical train must be placed within the enclosure. However, in a preferred CEOS instrument design, the entire optical train, and the optical bench on which it is mounted, would normally be situated within the temperature-controlled enclosure of the present invention, as shown on FIGS. 2a, 2b and 3. Processor 22 would not normally be placed inside the novel enclosure of the present invention. As previously indicated, gases other than dry air can be used in enclosure 30 to practice the invention, although dry air is normally the gas of choice.

What is claimed is:

1. Apparatus for maintaining an optical cavity of a cavity enhanced optical spectroscopy instrument at a substantially constant temperature, the apparatus comprising:
   a) an enclosure having interior and exterior wall surfaces, said enclosure surrounding said optical cavity, wherein said interior wall surfaces are spaced apart from said optical cavity;
   b) at least one heat exchanger positioned within said enclosure in proximity to at least one of said interior wall surfaces;
   c) at least one heat pump in thermal communication with both said heat exchanger and an ambient environment exterior to said enclosure;
   d) at least one fan positioned within said enclosure, said fan causing a portion of a gas contained within said enclosure to circulate in laminar flow following a path substantially along interior wall surfaces of said enclosure, whereby said flowing gas makes thermal contact with said heat exchanger, said optical cavity not being situated within said flow path;
   e) an optical bench supporting said optical cavity; and
   f) at least one temperature sensor affixed to said optical cavity or said optical bench.

2. The apparatus of claim 1, wherein there is present in said enclosure a plurality of heat pumps, heat exchangers and fans.

3. The apparatus of claim 1, wherein at least a majority of the components of the optical train of said cavity enhanced optical spectroscopy instrument are situated within said enclosure and not within said flow path.

4. The apparatus of claim 1, wherein there is at least a second temperature sensor affixed to said at least one heat exchanger.

5. The apparatus of claim 1, wherein said temperature sensor comprises a thermistor.

6. The apparatus of claim 1, wherein a layer of insulting material covers at least a substantial portion of at least one of the interior and exterior wall surfaces of said enclosure.

7. The apparatus of claim 1, wherein said heat exchanger comprises a metal structure having a plurality of fins positioned in said laminar flow path.

8. The apparatus of claim 1, wherein said heat pump comprises a Peltier Effect thermoelectric cooler.

9. The apparatus of claim 1, wherein said fan is driven by a DC electric motor.

10. The apparatus of claim 1, wherein said optical bench is affixed to a plurality of mounts, which mounts maintain said bench out of contact with said interior wall surfaces.

11. The apparatus of claim 10, wherein at least a portion of said mounts are positioned within said flow path.

12. The apparatus of claim 1, wherein said gas is dry air.

* * * * *